(12) United States Patent
Zollinger (10) Patent No.: US 10,430,758 B2
(45) Date of Patent: Oct. 1, 2019

(54) CYCLE COUNT BASED INVENTORY MANAGEMENT

(71) Applicant: Aesynt Incorporated, Cranberry Township, PA (US)

(72) Inventor: Christopher Zollinger, Gisbonia, PA (US)

(73) Assignee: Aesynt Incorporated, Warrendale, PA (US)

(*) Notice: Subject to any disclaimer, the term of this patent is extended or adjusted under 35 U.S.C. 154(b) by 1166 days.

(21) Appl. No.: 14/599,736

(22) Filed: Jan. 19, 2015

(65) Prior Publication Data

US 2016/0210589 A1    Jul. 21, 2016

(51) Int. Cl.
*G06Q 10/08* (2012.01)
*G06Q 50/22* (2018.01)

(52) U.S. Cl.
CPC ......... *G06Q 10/0875* (2013.01); *G06Q 50/22* (2013.01)

(58) Field of Classification Search
CPC ........................... G06Q 10/0875; G06Q 50/22
USPC .......................................................... 705/2
See application file for complete search history.

(56) References Cited

U.S. PATENT DOCUMENTS

| | | | | |
|---|---|---|---|---|
| 5,758,329 A | * | 5/1998 | Wojcik | G06Q 10/087 |
| | | | | 705/28 |
| 6,895,304 B2 | | 5/2005 | Spano, Jr. et al. | |
| 7,693,757 B2 | * | 4/2010 | Zimmerman | G06Q 10/00 |
| | | | | 235/462.11 |
| 7,720,569 B2 | | 5/2010 | Forrester et al. | |
| 7,766,242 B2 | | 8/2010 | Lunak et al. | |
| 8,723,674 B2 | | 5/2014 | Conley et al. | |
| 8,843,403 B2 | * | 9/2014 | Laub | G06Q 10/087 |
| | | | | 700/115 |
| 2002/0087436 A1 | * | 7/2002 | Guthrie | G01D 4/004 |
| | | | | 705/28 |
| 2004/0099683 A1 | * | 5/2004 | Shows | G06F 19/3462 |
| | | | | 221/263 |
| 2004/0133705 A1 | * | 7/2004 | Broussard | G06F 19/3462 |
| | | | | 710/1 |
| 2009/0012820 A1 | * | 1/2009 | Bishop | G06Q 10/087 |
| | | | | 705/3 |
| 2012/0317001 A1 | * | 12/2012 | DeBusk | G06Q 10/087 |
| | | | | 705/29 |
| 2013/0335563 A1 | * | 12/2013 | Jordan | H04N 7/183 |
| | | | | 348/143 |
| 2014/0156348 A1 | * | 6/2014 | Sinkel | G06Q 30/0605 |
| | | | | 705/7.31 |

* cited by examiner

*Primary Examiner* — Eliza A Lam
(74) *Attorney, Agent, or Firm* — The Webb Law Firm (57) ABSTRACT

A method, system, and apparatus of rule based assigning a cycle count to an inventory item for a set of medical items is disclosed. A no-touch inventory system operates using information regarding medication flow throughout a patent care facility and evaluates pertinent inventory criteria for each of a plurality of items in the inventory. The evaluation compares inventory criteria in an intelligent inventory system. A learning factor can be applied such that conditionally effects the selective category by assigning a schedule for the cycle count of the inventory.

12 Claims, 5 Drawing Sheets

CYCLE COUNT BASED INVENTORY MANAGEMENT

BACKGROUND OF THE INVENTION

Field of the Invention

This disclosure relates to inventory monitoring and dispensing devices and systems. Particularly, this disclosure relates to an apparatus for tracking an inventory of medical items used to treat patients in a hospital, clinic, or other like healthcare settings.

Description of Related Art

The treatment of patients in hospitals, clinics, and like medical settings usually involves the use of medical items and medications. These items may include consumable items, such as medications. Medical treatment may also involve other disposable items, such as dressings and bandages, or other medical equipment. Items implanted into the patient or used in conjunction with surgical procedures may also be used during the course of a patient's medical treatment. Examples of such items include splints, catheters, or guide wires which are normally used during cardiac catheterization or angioplasty. To serve the needs of its patients, a clinic or hospital must always maintain sufficient stocks of these items on hand. Further, as medical items and medications are often expensive, the charges associated with their use must be accurately billed to the patient.

Currently, most systems for tracking inventory items in a hospital or clinic environment involve manual cycle counting medical items. Cycle counting is an alternative to the usual way in which inventory is counted. Instead of conducting a taxing physical count, yearly or at more frequent intervals, of all the items in a medical facility, counting is conducted daily or weekly on some of the total number of items, such that all items are continuously counted, typically several times a year. Thus, cycle counting is a process of regular assessment of the inventory.

Because medical facilities are typically unable to regularly count all their inventory items cost effectively, medical facilities may cycle count a small portion of the inventory, for example, each day. Cycle counting a small portion of the inventory assists in assuring that inventory information is sufficiently accurate and any discrepancy is quickly identified and fixed. This process also helps to identify and investigate underlying issues that result in inventory record errors, thereby addressing the root cause of the problem. Depending on the size of the inventory, cycle counting enables a medical facility to count each inventory item more than once or twice a year on average. However, it is desirable to have systems, apparatuses, and methods for intelligently identifying inventory items in a medical inventory of a medical facility which should be cycle counted.

A number of medication and medical device tracking and inventory systems are known for use in pharmacies and hospitals. For example, a medication dispensing cabinet is disclosed in U.S. Pat. No. 6,895,304 to Spano, Jr. et al., which is assigned to the assignee of the present application and which is incorporated by reference in its entirety. The '304 patent discloses a dispensing cabinet and method of use. The cabinet includes a number of removable shelves enclosed in a housing and accessible through a lockable door. When the dispensing cabinet is in a dispensing mode, a user can open the door and remove an item to be obtained from one of the shelves. The user may enter the number of items taken from the cabinet at a terminal for inventory purposes. The user may be required to enter an identification code to cause the locked door to open. Once the desired items are removed from the shelves, the door returns to the locked position.

U.S. Pat. No. 8,723,674 to Conley et al. is directed to a tracking and inventory system that includes a medication dispensing cabinet. The cabinet is wirelessly connected to a server and computing device that can access and provide information associated with items stored in the dispensing cabinet. For example, the server and computing device may provide information about a patient's allergies, general health, or drugs previously administered. The information may be used to determine whether the drug should be provided to the patient. The cabinet may also include various sensing technologies to determine when an item is removed from the dispensing cabinet and to update inventory records accordingly.

Other patents in the field of automated inventor management include U.S. Pat. No. 7,766,242 to, Lunak et al. and U.S. Pat. No. 7,720,569 to Forrester et al., both incorporated herein by reference in their entirety.

SUMMARY OF THE INVENTION

A method of assigning a cycle count to an inventory item from a set of plural items is disclosed. The method may comprise steps of: 1) receiving, at an inventory system, information regarding the flow of medication throughout a patient care facility, and 2) evaluating one or more inventory criteria for each of a plurality of items of inventory, wherein the evaluation is a function of at least one of a similarity condition between the one or more inventory criteria and the selective category provided by an intelligent inventory system, and a learning factor, wherein the learning factor conditionally effects the selective category and assigns a schedule for the cycle count of the inventory item.

The method may further comprise assigning a specific cycle count for those medicines that are not assigned a scheduled count. The assigned specific cycle count may be a set randomized time and date. The method may additionally comprise assigning the cycle count to a technician, a group, or a location. The received information may be interface information from a hospital care system or a patient care facility. The received information may be medicine inventory information comprising one or more of pick or restock information. The similarity condition may be equal, greater, less than, increase, or decrease for medications. The selective category may be historical usage, previous count, average restock, or average pick. The information may be displayed on a handheld device of the medical technician. The display may be automatic as the technician enters definitional information for a specific medicine. The definitional information may be entered electronically by scanning a barcode or reading a tag.

An apparatus for use in a medication distribution environment is disclosed. The medication distribution environment may comprise an inventory management system comprising an algorithm for determining active medicines. The apparatus generally comprises a receiver for intake of a message comprising at least one count assignment for a medication inventory technician, a reader for reading information from a medicine container, and a display for prompting a cycle count based on the medicine information and at least one count assignment.

The display may include a display list, with the list comprising activation symbols for indicating completion of the cycle count. The apparatus may further comprise a link between the reader and the display. The apparatus may include an alarm to alert of variance to a user or technician, for example. The apparatus may include a controller for changing the settings of a cycle count. The change may comprise removing or adding medicine items from a schedule.

An inventory management system for providing medication inventory assignments from an inventory processor in accordance with input parameters in a patient care environment is further disclosed. The system may generally comprise a hospital care system comprising an interface for transmitting information over the interface, and an inventory processor for processing the information, updating a medicine record with at least part of the information, and providing a message with at least one cycle count assignment. Also, the system includes a medication processor comprising a receiver for intake of the assignment message, a schedule processor to prompt a user to update medicine information, a reader for reading information from a medicine container, and a display for prompting a cycle count based on the medicine information and at least one count assignment. In the inventory management system, the at least part of the information may be medicine inventory information, comprising one or more of pick or restock information. Also, in the inventory management system, the message may include instructions for multiple records.

Further details and advantages of the various aspects described in detail herein will become clear upon reviewing the following detailed description of the various embodiments in conjunction with the accompanying drawing figures.

DESCRIPTION OF THE INVENTION

The illustrations generally show preferred and non-limiting aspects of the systems and methods of the present disclosure. While the descriptions present various aspects of the apparatus and system, it should not be interpreted in any way as limiting the disclosure. Furthermore, modifications, concepts, and applications of the disclosure's aspects are to be interpreted by those skilled in the art as being encompassed, but not limited to, the illustrations and descriptions herein.

The following description is provided to enable those skilled in the art to make and use the described aspects contemplated for carrying out the disclosure. Various modifications, equivalents, variations, and alternatives, however, will remain readily apparent to those skilled in the art. Any and all such modifications, variations, equivalents, and alternatives are intended to fall within the spirit and scope of the present disclosure. Further, for purposes of the description hereinafter, spatial orientation terms, if used, shall relate to the disclosure as it is oriented in the drawing figures. However, it is to be understood that the disclosure may assume various alternative variations and step sequences, except where expressly specified to the contrary.

It is also to be understood that the specific devices and processes illustrated in the attached drawings, and described in the following specification, are simply exemplary aspects of the disclosure. Hence, specific dimensions and other physical characteristics related to the aspects disclosed herein are not to be considered as limiting. For the purpose of facilitating understanding of the disclosure, the accompanying drawings and description illustrate preferred aspects thereof, from which the disclosure, various aspects of its structures, construction and method of operation, and many advantages may be understood and appreciated.

Figure 1:
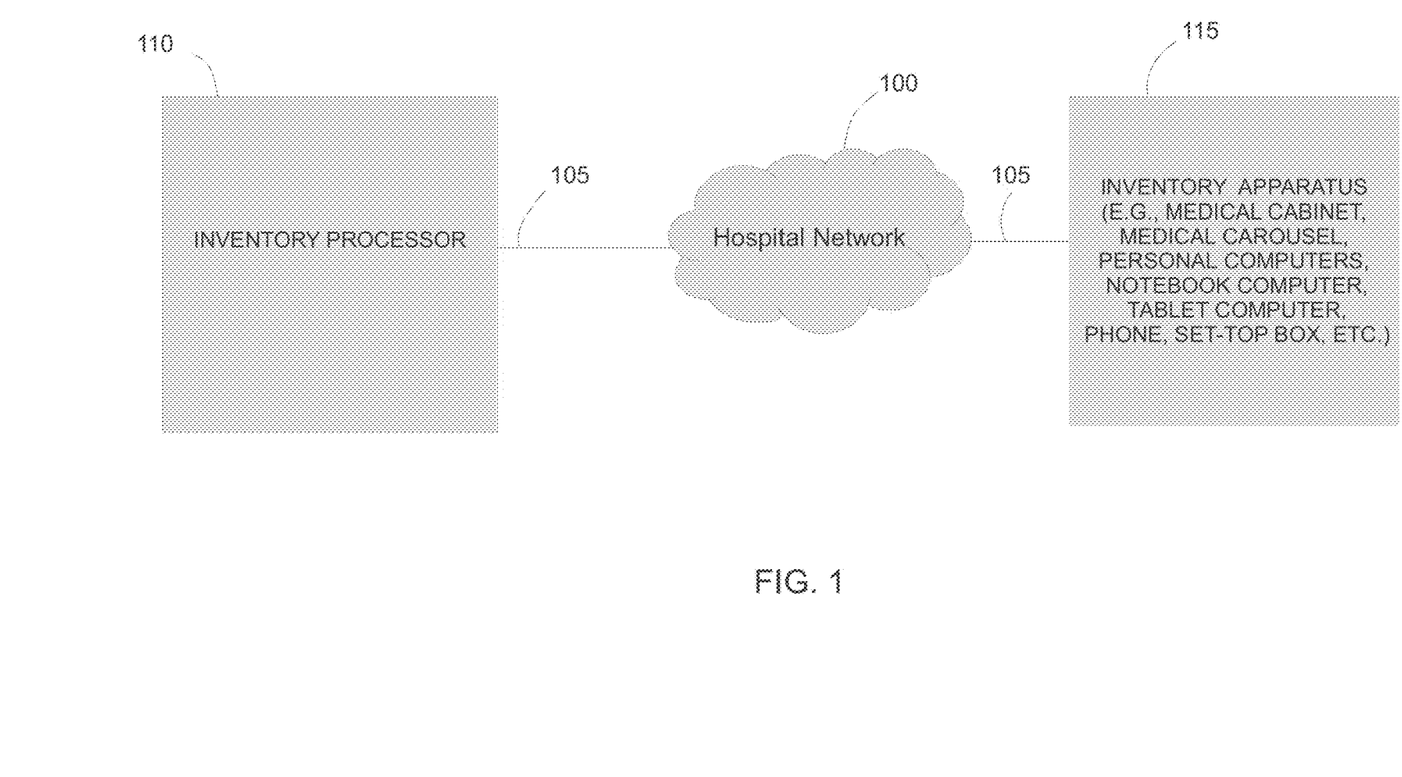
FIG. 1 is a schematic diagram of a network based system for cycle count management, in accordance with an aspect of the present disclosure.

In the illustrative arrangement of FIG. 1, an inventory apparatus 115 may be connected via links 105 to network 100. Inventory processor 110 may provide cycle count lists, instructions, or other medicine information to hospital inventory apparatus 115 for technicians. Likewise, information including cycle counts, may be provided back to inventory processor 110 from inventory apparatus 115. Inventory technicians are responsible for maintaining inventory throughout a hospital care environment. Actual inventory must match the predicted inventory based on medicine orders. The medicine orders are input by hospital care workers and expected to match exactly the actual picks and restocks of medicine. Medicine can be dispensed via many different forms, for example, pills, bottles, vials, packages, or any other dispensing mode known in the art. Each unit of medicine ordered relates to an item that is taken or placed into inventory and must be tracked. The picker or stocker can be forced to count and update inventory at the time of dispensing, however this can introduce certain inefficiencies. In one aspect of the invention, the picker and stocker may update the actual inventory without applying an update to the inventory apparatus 115. An intelligent cycle count system is then used to determine and assign the items for counting.

Inventory apparatus 115 may include devices known in the art or any combination of devices suitable for providing access to inventory technicians of the systems and methods of the present disclosure. Inventory apparatus 115 may include, for example, any suitable personal computer (PC), network enabled cabinet or carousel, portable computers (e.g., a notebook computer), handheld tablet computers, personal digital assistant (PDA), cellular phone, set-top box (e.g., a Web TV enabled set-top box), or other device suitable for providing access to a network 100.

Inventory processor 110 may be servers suitable for processing medicine inventory information received from hospital inventory apparatus 115. Inventory processor 110 may, for example, provide one or more interfaces to inventory apparatus 115 using suitable protocols. Access may include scripts, computer code, or subsets of computer code that define mini-programs or interface calls directed to applications. The interfaces may be provided to send and receive data for use by technicians using inventory apparatus 115. The data is in the form of messages for prompting technicians for cycle counts of specified medicine or other hospital inventory. The messages may be lists of medicine with corresponding schedules and expected counts. Inventory processor 110 may run a database engine suitable for maintaining electronic databases, such as Microsoft SQL Server, Oracle 8i, or any other suitable database engine. Inventory processor 110 may maintain medical item databases, such as databases for pharmaceutical products or any other suitable medical product or combination of products. Information received by the inventory processor 110 may be written to the database through methods known in the art.

Figure 2:
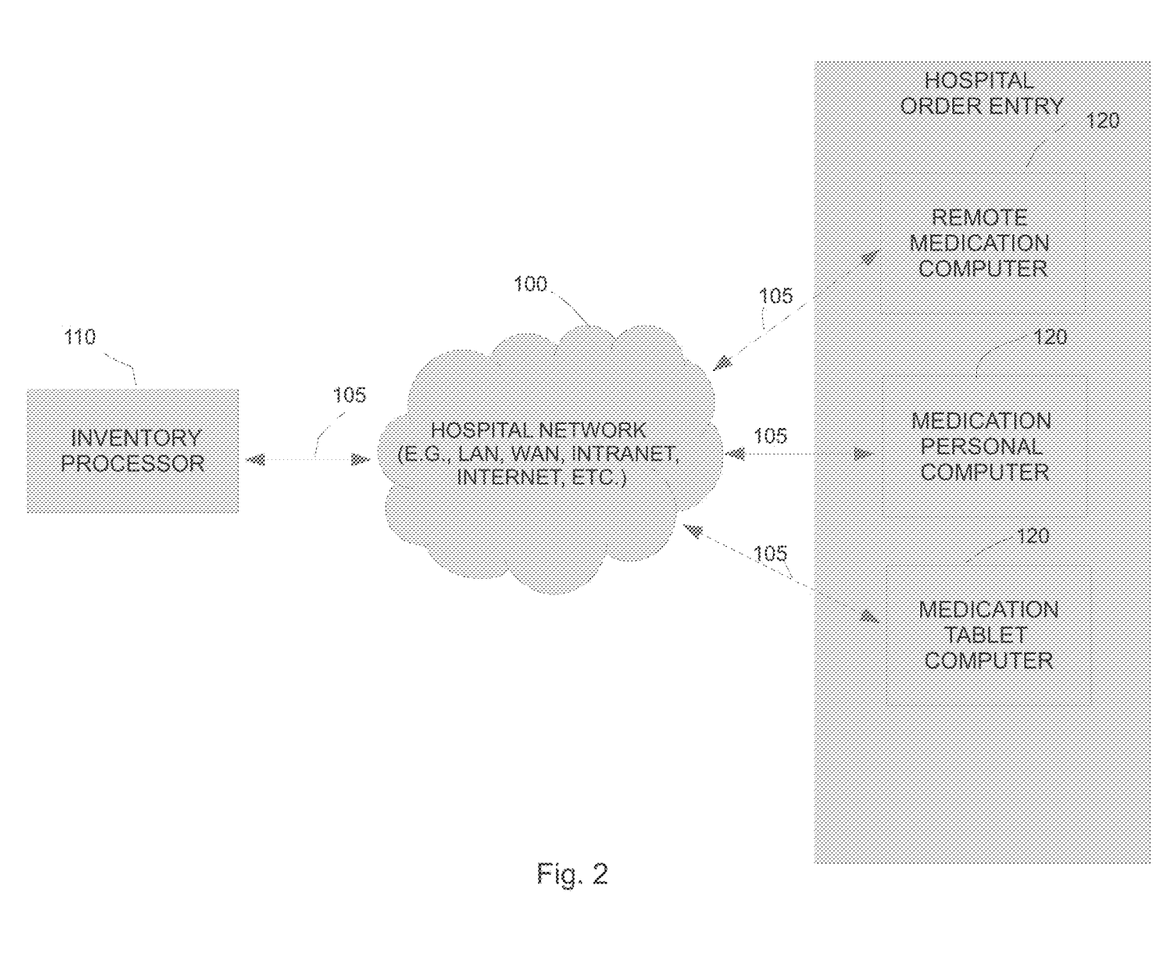
FIG. 2 is a schematic diagram of an access device used in FIG. 1, in accordance with an aspect of the present disclosure.

FIG. 2 shows another illustrative arrangement for a system in accordance with an aspect of the present disclosure. In the network arrangement of FIG. 2, order entry computers 120 are interconnected via network 100 to hospital inventory processor 110. Hospital inventory processor 110 may further include systems and software suitable for allowing users to perform hospital inventory management. Hospital inventory processor 110 may, for example, maintain drug distribution and inventory management information from order entry computers 120 within a hospital. Order information regarding medical inventory of products can be entered by doctors, nurses and other hospital staff, as medicine is needed for patients. The orders are entered into the system using order entry computers 120 and then transferred to inventory processor 110 to determine inventory requirements. Such order information may be received as, for example, medicine picks, restocks, date, time, location, type, name, lot, etc.

Hospital communications network 100 may be any suitable local area network (LAN), wide area network (WAN), or other suitable network. Order entry computers 120 may provide users with access to web enabled hospital inventory pages from a hospital server. Medical products can be automatically delivered to an area of use or requested on demand using hospital inventory processor 110. An area of use may be the place where commonly stocked items are stored. The area is potentially composed of medical wards, clinics, and specialists, while the area of use would be, for example, open shelves, or medical cabinets and carts within those areas. In addition, hospital inventory processor 110 may provide hospital care workers using hospital care order entry computers 120 with up-to-date medical stock information about quantity, expiry, batch, and location as received via interfaces from the hospital inventory processor 110.

Inventory processor 110 may provide other beneficial uses, for example, it allows the user to enter manufacturing and expiry dates for the item during receiving or stocking. For about-to-expire items, the inventory processor 110 can trigger an alert to notify the user before the items are expired so that proper actions or counter-measures can be taken. The system does not allow items that already expired to be used and prompts actions, such as removal from the storage rack or return to the manufacturer for exchange. Hospital inventory processor 110 directs the user to a location for items to be stored during restock or which specific location for items to be located for picking. Hospital inventory processor 110 also can track and report on demand patterns, stock movement (Fast, Slow, or Not Moving), and medicine history, e.g., quality, recall, or expiry.

Figure 3:
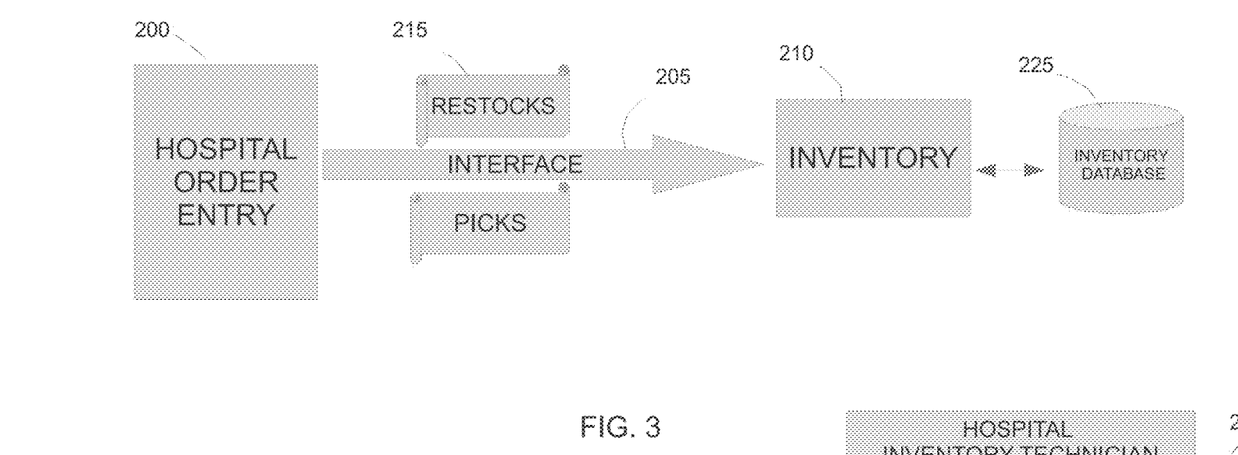
FIG. 3 is a schematic diagram of an interface of stocking information to a hospital inventory system as shown in FIG. 2, in accordance with an aspect of the present disclosure.

FIG. 3 shows a generalized arrangement for the interface of stocking information about medicine in a location, such as a medicine open shelf system, from hospital care computers to the hospital inventory apparatus 115 of FIG. 2. In the depicted arrangement, order entry system 200 collects information about picks and restocks for an open shelf system. This information is stored in order entry system 200 or a central storage system until stored information is sent through an inventory interface 205 to an inventory processor 210. The same process may utilize real-time capable processing. The medicine open shelf is an example of a medicine dispensing system. The order entry system 200 can receive order information about any system configured dispense medicine carts, cabinets, carousels, and other storage devices. Integration of information can be handled using communication platforms between nodes, such as application programming interfaces or messaging platforms, or queueing mechanisms to transmit messages between disparate systems. A cycle counting algorithm uses the received information from order entry system 200.

In the network of FIG. 3, interface 205 transmits medicine order information, such as updates 215. The updates 215 are information about the predicted flow of information from a particular location or device. This information can be used to obtain a predicted count for a location or device at a specific time. These updates 215, with restock and pick data, may be automatically generated and may be automatically transmitted by interface 205 as medicine counts change or on a scheduled basis. The updates 215 are received by the inventory processor 210 and stored in an inventory database 225. The inventory interface 205 information is relevant to the flow of medicine throughout the hospital, or like medical facility, and gives an accurate prediction to the inventory database 225 of what medicine is incoming and outgoing.

Figure 4:
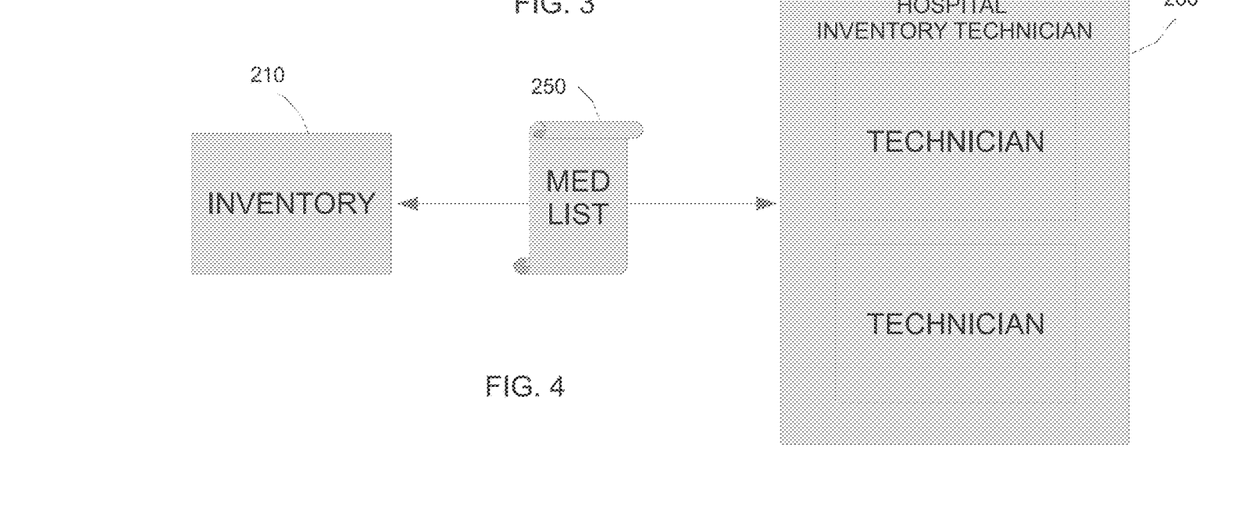
FIG. 4 is a schematic diagram for showing interface inventory information to a technician, in accordance with an aspect of the present disclosure.

FIG. 4 shows a generalized arrangement for interface inventory information to pass to a technician 260. In the network of FIG. 4, the inventory processor 210 transmits medicine cycle count assignment information from the inventory apparatus 115 shown in FIG. 1 via a medicine list 250 to the hospital inventory technician 260. The technician 260 is exemplary and is not meant to be limiting, as one skilled in the art could envision a team of technicians that use the system 115 to share worklists appropriately. The technician 260 manages worklist items, and performs cycle counts, using an order entry computer 120 as shown in FIG. 2. Cycle count information is then transmitted to the inventory processor 210 from the technician 260 using the same path in an exemplary system, however, the information may be batched in the device or a proxy system until transmission. In one aspect, the technician 260 uses an inventory apparatus, such as a remote handheld computer configured to wirelessly attach to an order entry computer 120 or hospital network. With reference to FIG. 1, an inventory apparatus 115 device may include a transmitter and receiver for sending and receiving messages and intake of medicine list messages. The inventory apparatus 115 device provides software for showing a list, indicating a schedule, and intake of cycle count information. A schedule is used by the processor to indicate to a user to update medicine information based on criteria in the medicine list 250. The inventory apparatus 115 device provides a reader for machine readable information from a medicine container, e.g., RFID tags, barcode, or QR codes. The inventory apparatus 115 device also provides a display and input apparatus for prompting the technician for a cycle count based on the medicine information and at least one count assignment. The inventory apparatus 115 device can also be specially programmed using computer code to operate on received information.

The medicine list 250 is a cycle count list compiled by the inventory processor 210 and used by the inventory processor 210 for assigning a cycle count to the technician 260. Medicine list 250 includes assignments for a cycle count in a certain location or dispensary device for any identified medical items requiring cycle counts, about which information is stored in the inventory processor 210. The cycle counting algorithm ensures that each of the medical items in the medicine list 250 are counted only as needed, e.g., on a set schedule. Intelligent cycle counting may be used, where cycle counts are performed based on compliance information. One such intelligent cycle count uses frequency information, i.e. a new count is only performed when the number of compliant cycle counts reaches a certain limit. In one aspect, after a specified medicine is compliant for example, a limit could be set at three, then, after three times, the medicine is placed on the compliant list and is only checked randomly. Intelligent cycle counting brings an overall accuracy to the inventory data and significantly improves the inventory management for the medical facility, as it limits the counting to only a set of focused medical items, such as based on inventory flow, and not those medical items which remain stagnant. The flow is the amount of medicine that is restocked or, alternatively, used. The features and aspects in this disclosure are suitable for improving the efficiency of assessment of inventory, providing hospitals with the ability to bypass counts on picks. This cycle count system provides inventory counts of the operation and supply of products, reducing late or early replenishment of the inventory. Since only the most critical medical items are counted, it enforces the accuracy of the cycle count.

Figure 5:
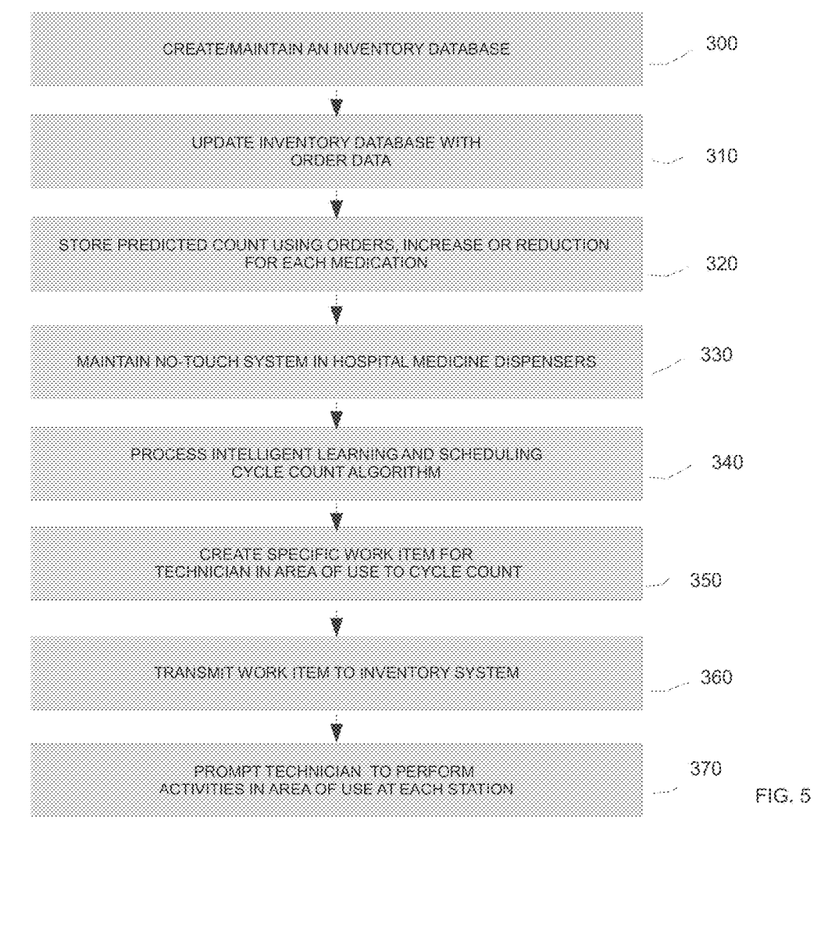
FIG. 5 is a generalized flowchart of illustrative steps involved in assigning cycle count worklist items, in accordance with an aspect of the present disclosure.

In one aspect, the hospital care facility utilizes a no-touch medicine inventory system that processes orders for the restock and pick updates 215 to determine predicted medicine counts for each location and uses cycle counts as needed to confirm the predicted count information. FIG. 5 shows the steps performed by the apparatus and systems described herein. In step 300, an inventory database is created and maintained by the inventory processor 210. The inventory database may store medicine data, location data, and personnel data.

Next, in step 310, the inventory database is updated automatically each time an order is placed. An interface may be used to transfer information about orders from the hospital order entry system 200 to the inventory processor 110, as shown in FIG. 2. The orders are entered into the hospital network by hospital care technicians using order entry computers 120. In one aspect of the system, the inventory system relies on the order information for stocking purposes. At step 320, the order information is used to calculate the count for ordered medicines. If an order is placed for restock, the medicine automatically increases in the inventory database. Likewise, if an order is placed for a pick, the system automatically decreases. This information is used as the predicted count that is expected on the shelf.

Next, at step 330, in one aspect of the system, a no-touch system is implemented, where a medicine picker may pick medicine from open shelves, or any medicine dispenser, as needed, with no data entry required, and the picker is not expected to count or update inventory at the time of dispensing. At step 340, inventory technicians reporting actual inventory throughout the hospital care environment, to ensure the actual inventory count matches the predicted inventory count, are intelligently scheduled cycle count assignments. Medicine can be dispensed via many different forms, for example, pills, blister packs, bottles, vials, packages, or any other dispensing mode known in the art. A cycle count algorithm of the inventory processor schedules cycle counts as needed. For example, if an order is placed for five pills, but the pills come in blister packs of six, the picker may take the entire blister pack, causing a discrepancy between the order and the pick. When the cycle count is performed, the predicted would not match the actual count, which may cause the inventory processor to assign a cycle count.

With continuing reference to FIG. 5, at step 350, as a result of the cycle count algorithm, work items are created and assigned to technicians 260, each compiled into a message and sent to the technician 260. Next, at step 360, the inventory processor 210, as shown in FIG. 4, transmits medicine cycle count assignment information, using a medicine list 250 or some other transport structure, from the inventory processor 210 to the hospital inventory technician 260. The technician 260 or a team of technicians that use the apparatus 115 may then share worklists appropriately. The technician 260 may manage worklist items using an order entry computer 120 as shown in FIG. 2.

Finally, at step 370, a technician 260 receives the worklist using software applications on a handheld computer. The worklist is assigned to a technician corresponding to the particular location for flow purposes. Using an inventory apparatus, such as a handheld device, a receiver operates a medicine list 250 message. As the technician 260 makes rounds for cycle counting, the handheld provides the items to be counted. The items can be based on the location of the technician 260 in the hospital, either using GPS, by scanning locations, or by manual entry. The handheld display is programmed to show a worklist of medicine for cycle counting and includes input mechanisms for manipulating the items on the worklist. An internal processor is provided to run software and analyze the medicine worklist 250 in order to prompt a user to update medicine information based on criteria in the medicine list 250. The software can be used to further conditionally prompt a user on the display, provide presentation information, and respond to query requests about medicine. The software may be configured to hide or display expected cycle count results. The technician 260 may scan medicine containers and shelf locations using the handheld reader of machine readable information. The handheld display comprises a user interface with activation symbols for indicating to the apparatus and applications processing completion of cycle count. Other aspects allow the technician 260 to change the cycle count worklist, such as by removing or adding medicine schedules, modifying the schedule, or updating with a new medicine. The inventory apparatus can include an alert, for example to alert a user of an input variance.

Figure 6:
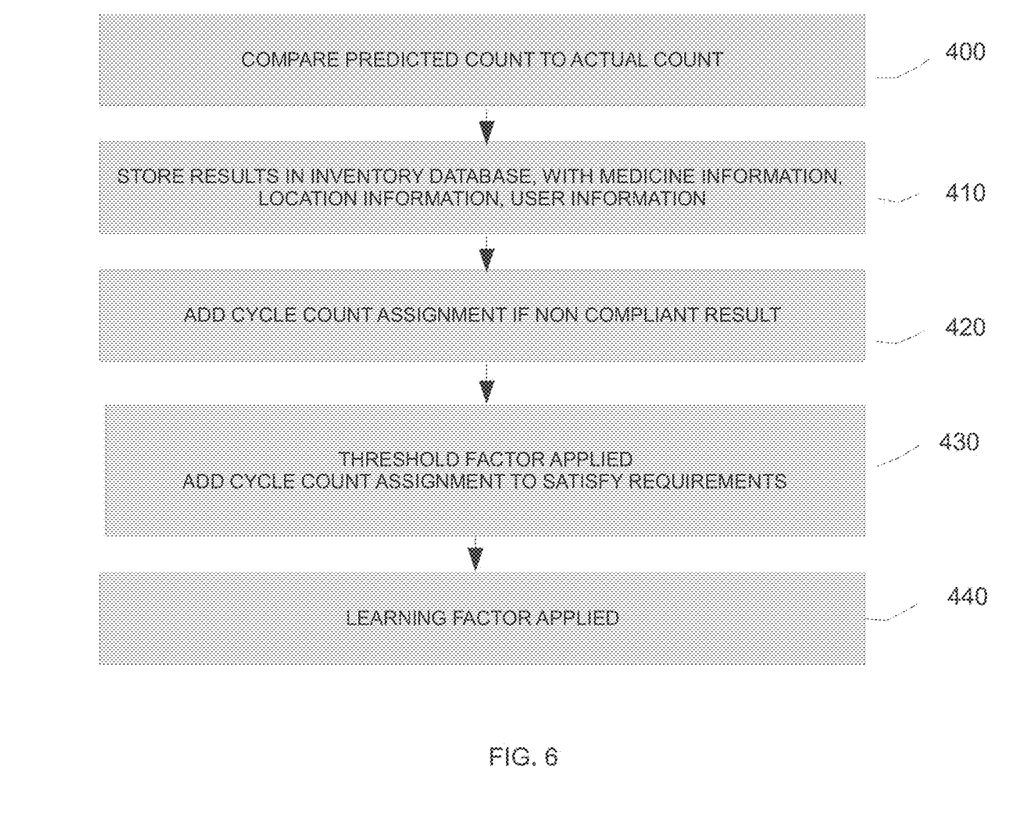
FIG. 6 is a generalized flow chart of illustrative steps involved in an exemplary cycle count algorithm.

FIG. 6 shows further details of a cycle count algorithm of the inventory processor in accordance with an aspect of the invention. In one aspect, the inventory processor 210 includes a cycle count algorithm that processes the medicine updates 215 from the inventory technician to determine medicine assignment information for cycle counts. FIG. 6 shows the steps performed by the apparatus and systems described herein.

At step 400, inventory processors compare predicted counts to actual count. Inventory technicians are responsible for maintaining inventory throughout a hospital care environment. Actual inventory must match the predicted inventory based on medicine orders. Actual inventories are determined when the technicians send cycle count data for medicine back to the inventory processor. The medicine orders are input by hospital care workers and expected to match exactly the actual picks and restocks of medicine. The internal programming determines if the predicted count matches the actual count. If it does not, the medicine may be added to a cycle count assignment. If the actual count is in line with expectations, the medicine may still be counted depending on other factors in the process. When an assignment is given to staff to perform a cycle count of a specified medicine, such as the technician 260 as shown in FIG. 4, or a group of technicians who are capable of performing a cycle count on particular medicines, they may be assigned as work items. Alternatively, other modes of communication may be adapted to notify technicians of cycle counts.

At step 410, the results of the test in step 400 may be stored in the inventory database, with medicine data, location data, and user data. The results are stored for historical purposes to provide information about medicine. The information may be used by the processor to intelligently determine if a cycle count is required.

At step 420, cycle count assignments may be created if a medicine is determined to be non-compliant. Items can be evaluated by comparing inventory criteria to reach a determination, such as equal, greater, less than, increase, decrease, period of time, duration, aggregate, average, etc., as compared to the combined restock and pick updates. In one aspect, if the medicine increased in count based on a similarity condition, such as a range or hard limit, then a medicine item is added to an assignment medicine list. Likewise, the medicine can be added for both increase and decrease.

At step 430, in an exemplary aspect, for those having met the predicted count, other requirements may exist. For example, if the number of days since the last cycle count is inside a threshold, no processing of additional cycle count is scheduled. Stagnant items may also not require a scheduled cycle count. The stagnant items may be scheduled separately, at times determined by the system. These items can be accounted using an ad hoc or specific time to optimize the work patterns of the technician 260. One such optimization is to match the stagnant items with nearby scheduled items, thereby prompting the technician 260 to cycle count both a scheduled item and stagnant item at essentially the same time. In another aspect, randomizing the schedule for the stagnant items provides coverage for cycle count of the remaining set of items.

At step 440, a learning factor may be used by the inventory processor 110 to further specify a worklist for cycle counts. For example, the system may determine if instances of staff mishandling reports exist, or if staff is on a watch list. Also, if types of medicine or medicine packing causes problems, it may be placed on a watch list. For example, blister packs may be known to have been misreported frequently. The learning factor can comprise a ceiling established where the increase or decrease reaches a limit. For example, medicine counted during the last cycle count is within the range and the cycle count is not required. A learning factor can also, in one aspect, use the number of times in the course of a month a specific medicine item has been on the list. Since the item has been on the list for an extended period, the learning factor determines that the medical item should remain on the cycle count for a certain period of time regardless of the selective criteria, e.g., a week, a month, or a quarter.

While aspects of a cycle count based inventory management unit, system, and methods associated therewith were provided in the foregoing description, those skilled in the art may make modifications and alterations to these embodiments without departing from the scope and spirit of the disclosure. Accordingly, the foregoing description is intended to be illustrative rather than restrictive. The disclosure described hereinabove is defined by the appended claims and all changes to the disclosure that fall within the meaning and the range of equivalency of the claims are to be embraced within their scope.

The invention claimed is:

1. A method for managing medication inventory comprising:

maintaining, in a medication dispensing device in a dispensing mode, a medication a no-touch system where a medication is picked from the medication dispensing device without updating an inventory count of the medication in an inventory system;

receiving, with a computer system comprising one or more processors, an order to one of increase the inventory count of the medication in the inventory system and decrease the inventory count of the medication in the inventory system from an order entry device other than the medication dispensing device;

dispensing device in the dispensing mode;

determining, with the computer system, a predicted count of the medication associated with the medication dispensing device based on the order;

determining, with the computer system, assignment data associated with the medication based on the predicted count and one or more inventory criteria associated with the medication;

providing, with the computer system, the assignment data to a remote device, wherein the assignment data includes a prompt to perform a cycle count of the medication associated with the medication dispensing device;

receiving, with the computer system from the remote device, cycle count data associated with the cycle count of the medication; and updating, with the computer system, the inventory count of the medication based on the cycle count data.

2. The method as in claim 1, wherein the one or more inventory criteria is associated with a threshold for the predicted count of the medication that is equal, greater, or less than a combined count of the medication associated with a plurality of medication dispensing devices.

3. The method as in claim 1, wherein the one or more inventory criteria is associated with a historical usage of the medication, a previous count of the medication, an average restock time of the medication, or an average pick time of the medication.

4. The method as in claim 1, further comprising:

displaying, with the remote device, the prompt to perform the cycle count of the medication to a medic al technician.

5. The method as in claim 4, wherein the display of the prompt is performed automatically in response to the remote device receiving definitional information associated with the medication from the medical technician.

6. The method as in claim 5, wherein the definitional information is received by the remote device via electronically scanning a barcode or reading a tag with the remote device.

7. A medication inventory management system comprising:

a medication dispensing device maintained in a no-touch system where a medication is picked from the medication dispensing device without updating an inventory count of the medication in an inventory system; and a computing system comprising one or more processors, wherein the one or more processors are programmed or configured to:

receive an order to one of increase the inventory count of the medication in the inventory system and decrease the inventory count of the medication in the inventory system from an order entry device other than the medication dispensing device;

determine a predicted count of the medication associated with the medication dispensing device based on the order;

determine assignment data associated with the medication based on the predicted count and one or more inventory criteria associated with the medication;

provide the assignment data to a remote device, wherein the assignment data includes a prompt to perform a cycle count of the medication associated with the medication dispensing device;

receive from the remote device, cycle count data associated with the cycle count of the medication; and update the inventory count of the medication based on the cycle count data.

8. The system as in claim 7, wherein the one or more inventory criteria is associated with a threshold for the predicted count of the medication that is equal, greater, or less than a combined count of the medication associated with a plurality of medication dispensing devices.

9. The system as in claim 7, wherein the one or more inventory criteria is associated with a historical usage of the medication, a previous count of the medication, an average restock time of the medication, or an average pick time of the medication.

10. The system as in claim 7, further comprising:
the remote device programmed or configured to display the prompt to perform the cycle count of the medication to a medical technician, wherein the remote device is a mobile device programmed or configured to wirelessly communicate with the computing system.

11. The system as in claim 10, wherein the display of the prompt is performed automatically in response to the remote device receiving definitional information associated with the medication from the medic al technician.

12. The system as in claim 11, wherein the definitional information is received by the remote device via electronically scanning a barcode or reading a tag with the remote device.

* * * * *

UNITED STATES PATENT AND TRADEMARK OFFICE
CERTIFICATE OF CORRECTION

PATENT NO. : 10,430,758 B2  
APPLICATION NO. : 14/599736  
DATED : October 1, 2019  
INVENTOR(S) : Christopher Zollinger Page 1 of 1

It is certified that error appears in the above-identified patent and that said Letters Patent is hereby corrected as shown below:

On the Title Page

Item (72), Inventor first line, delete "Gisbonia," and insert -- Gibsonia, --

In the Claims

Column 10, Line 1-2, Claim 1, delete "device in a dispensing mode, a medication" and insert -- device, --

Column 10, Line 12, Claim 1, below "device;" delete "dispensing device in the dispensing mode;"

Column 10, Line 44, Claim 4, delete "medic al" and insert -- medical --

Column 10, Line 51-52, Claim 6, delete "electronic ally" and insert -- electronically --

Column 12, Line 15, Claim 11, delete "medic al" and insert -- medical --

Signed and Sealed this  
Seventh Day of January, 2020

Andrei Iancu  
*Director of the United States Patent and Trademark Office*